United States Patent [19]
Wilson

[11] 3,975,517
[45] Aug. 17, 1976

[54] ENTERIC DISEASE VACCINE

[75] Inventor: Michael R. Wilson, Guelph, Canada

[73] Assignee: Canadian Patents and Development Limited, Ottawa, Canada

[22] Filed: Mar. 19, 1975

[21] Appl. No.: 559,762

Related U.S. Application Data

[62] Division of Ser. No. 256,977, May 25, 1972, Pat. No. 3,907,987.

[52] U.S. Cl. .................... 424/87; 424/92; 424/93; 426/583; 426/585
[51] Int. Cl.² .................... A61K 39/40; A23C 9/00; A23C 21/00
[58] Field of Search .................. 424/87, 92, 93; 426/583, 585

[56] References Cited
UNITED STATES PATENTS

| | | | |
|---|---|---|---|
| 2,110,208 | 3/1938 | Eggert | 424/92 |
| 3,127,318 | 3/1964 | Eversole et al. | 424/92 X |
| 3,128,230 | 4/1964 | Heinbach | 424/92 X |
| 3,376,198 | 4/1968 | Peterson et al. | 424/92 X |
| 3,907,987 | 9/1975 | Wilson | 424/92 |

OTHER PUBLICATIONS

Wilson et al., Vet. Bul. 41(12), No. 6106, Dec. 1971.
Wilson et al., Vet. Bul. 42(3), No. 1159, Mar. 1972.
Svendson et al., Vet. Bul. 42)3), No. 1154, Mar. 1972.
Wilson et al., Vet. Bul. 42(12), No. 7100, Dec. 1972.
Wilson, Vet. Bul. 43(4), No. 1451, Apr. 1973.

*Primary Examiner*—Shep K. Rose
*Attorney, Agent, or Firm*—Alan A. Thomson

[57] ABSTRACT

Preparation of and live bacterial vaccine from selected strains of *Escherichia coli*. The bacterial cells are treated with dilute formalin solutions (about 0.02 to about 0.08% v/v formalin) for a period to modify the bacteria without inactivation thereof. One preferred strain is EW1 serogroup of 0157. The vaccine has been found particularly effective in preventing the occurrence of enteric colibacillosis in newborn animals. A preferred technique is to vaccinate cows, recover the milk, and continually feed it as a milk replacer to the newborn during the susceptible period.

5 Claims, No Drawings

ENTERIC DISEASE VACCINE

This is a division of application Ser. No. 256,977 filed May 25, 1972, now U.S. Pat. No. 3,907,987.

This invention deals with bacterial vaccines from *Escherichia coli*, their preparation and use. A formalinized live vaccine is prepared from selected strains.

A number of vaccines have been prepared from *E. coli* but in most cases immunity has not been clearly shown (control or non-vaccinated animals were not kept in parallel). Well-controlled field trails with many vaccines gave no indication of protection. Inconsistent results with *E. coli* vaccines and the immunological treatment of *E. coli* — associated enteritis have caused confusion.

Vaccines have been prepared from *E. coli* by growth on agar surfaces and washing off the live cells (the vaccine is free of culture and growth by-products). Use of these active cells as vaccines is believed to carry many risks e.g. infection, severe reaction, possible abortion etc. Formaldehyde has been used to inactivate bacterial cultures but the amount of formaldehyde and severity of treatment has been sufficient to kill the cells and to substantially alter the cell constituents. The antigenicity is believed to be adversely affected or decreased when the cells are killed in this manner. Formaldehyde has been used in vaccine preparation, but always to inactivate the bacteria.

It would be desirable to prepare *E. coli* vaccines with the full antigenic content associated with live cells yet without the risks associated with active pathogenic bacteria.

It has now been found according to this invention that a relatively safe and effective vaccine for coliform enteritis and related infections can be prepared by a controlled formalinization (or incomplete formaldehyde treatment) of selected *E. coli* strains. A broth culture of the *E. coli* bacteria is incubated for about 2 to about 20 hours in the presence of about 0.02 to about 0.08% (vol./vol.) formalin (0.008 to 0.032% wt./vol.) formaldehyde). The cell and colony growth are obviously modified (change in appearance, growth pattern and antigenic effect) yet many remain viable and are able to gradually recover their normal growth.

The vaccine normally contains the entire broth culture constituents including metabolic waste products and extracellular proteins. During incubation with formalin the culture concentration is suitably about $10^8$ to about $10^9$ viable organisms per ml. the count decreasing on incubation. The formalinization reduces the number of colony-forming units to approximately 3 log dilutions or more (e.g. (2–7) lower than are in the starting broth culture. This incubated broth is then usually administered without further dilution as the vaccine with at least about $10^2$ viable organisms per ml.

The effect of varying concentrations of formalin is illustrated in Example 1. Below about 0.02% v/v formalin, the bacteria were not significantly affected, and above about 0.07–0.08% all were dead. About 0.04% v/v formalin (or about 0.016% w/v formaldehyde) has been found to be a desirable concentration with a minimum of infectivity or side effects and yet with high antigenic titer. Formalin itself is a 40% aqueous solution of formaldehyde (wt./vol.).

The time of incubation with formalin may range from about 2 to about 20 hours, preferably about 10–15 hours. Below about 2 hours, the effect on the bacteria is inadequate, while above about 20 hours the inactivation becomes too great (lower antigenicity) and the benefit is not achieved. For the shorter times it is preferred to use the higher formalin concentrations, with 0.03–0.05% formalin for 10–15 hours being very suitable.

The selected *E. coli* strain is grown in a standard broth culture medium under aerobic conditions. Tryptic soy broth has been found satisfactory but other liquid media such as peptone broth, a supplemented yeast extract etc. may be used. (Suitable growth media for *E. coli* are known in the art). The bacteria may be maintained on solid media and the cells removed and suspended in a broth medium for the incubation.

One preferred strain of *E. coli* is EW1 serotype 0157:KV17 which has been found to be very susceptible to formalin and to give a vaccine having polyvalent antigenicity. This strain is being maintained at the Ontario Veterinary College, Dept. of Clinical Studies, University of Guelph, Ontario. Other strains are operative and can be selected for use in certain areas where they are responsible for known infections. Mixtures of strains can be used to obtain a degree of polyvalent effect, although the effect is not additive.

The storage of the vaccine must be controlled and ability of the treated bacteria to gradually recover normal growth and activity taken into account. It is not advisable to store the vaccine at room temperatures for longer than about 3 days. Cold temperatures e.g. 4°C can prolong the storage life for several weeks or longer. The vaccine has been lyophilized and stored at about 4°C for 3 months without significant change.

The vaccine can be administered or injected parenterally (e.g. intramuscular, intramammary, subcutaneous). Dosage of the vaccine will usually vary from about 1 to about 8 ml at concentrations raging from about $10^2$ to $10^7$ viable bacteria per ml. This corresponds to about 0.02 to about 0.05 g of lyophilized material per ml and dosages of the order of 1 mg per kg. of body wt. A 2 ml dose for sows has been found adequate. Up to 20 ml has been administered to cows but 4 ml. is usual. The dosage does not appear to be sharply critical. A series of 3 doses is recommended at intervals of about 1 to 2 weeks between doses, e.g. for sows about 4 weeks, 2 weeks and 1 week before farrowing. Where milk is being drawn from a vaccinated animal, the protective effect can be maintained in the milk by doses repeated at intervals.

The vaccine was evaluated by vaccinating sows and studying the serologic response, and by feeding colostrum, milk or serum from vaccinated sows to piglets exposed to infection under controlled conditions. Cows have also been vaccinated and the antibody activity and protective value of their milk evaluated. Good protection in piglets was obtained by feeding them whey from vaccinated milk cows. Milk from vaccinated cows has been spray-dried and reconstituted without apparent loss of protective effect.

The following Examples are illustrative.

EXAMPLE 1

Two strains of *E. coli* were selected i.e. the EW1 strain of 0157:KV17 and the P307 strain of 08;K87.88a,c. These strains were cultured in Tryptic Soy Broth and incubated for 15 hours at 37°C before treatment with various concentrations of formalin.

Formalin was added to the 15-hour broth cultures to give concentrations of from 0.01 to 0.1% v/v in 0.01% steps, and from 0.1 to 0.5% in 0.1% steps. The incubation in formalin was for the following times: 10, 15, 20 hours. Bacterial counts were then performed, the number of colonies per ml. being present on the culture plate were counted 24, 48 and 72 hours from the finish of the formalin incubation.

The results are shown in Tables 1 and 2.

Table 1

Number of Colonies of Strain P 307

| Conc. Formalin % v/v * | Hrs. of Incubation | Hours Incubation with Formalin | | | |
|---|---|---|---|---|---|
| | | 10 | 15 | 20 | 0 |
| 0.01 (0.004) | 24 | 3.0 × 10$^7$ | 7.1 × 10$^7$ | 6.9 × 10$^7$ | |
| | 48 | 4.0 × 10$^7$ | 7.7 × 10$^7$ | 6.8 × 10$^7$ | |
| | 72 | 3.9 × 10$^7$ | 7.2 × 10$^7$ | 6.6 × 10$^7$ | |
| 0.02 (0.008) | 24 | 7.9 × 10$^6$ | 6.6 × 10$^6$ | 6.9 × 10$^6$ | |
| | 48 | 8.1 × 10$^6$ | 7.3 × 10$^6$ | 6.7 × 10$^6$ | |
| | 72 | 8.1 × 10$^6$ | 7.4 × 10$^6$ | 6.7 × 10$^6$ | |
| 0.03 (0.012) | 24 | 3.0 × 10$^5$ | 1.8 × 10$^5$ | 3.5 × 10$^5$ | |
| | 48 | 4.1 × 10$^6$ | 3.9 × 10$^6$ | 2.7 × 10$^6$ | |
| | 72 | 4.1 × 10$^6$ | 3.8 × 10$^6$ | 3.0 × 10$^6$ | |
| 0.04 (0.016) | 24 | 0 | 0 | 0 | |
| | 48 | 7.3 × 10$^5$ | 2.1 × 10$^5$ | 7.5 × 10$^4$ | |
| | 72 | 1.4 × 10$^6$ | 4.3 × 10$^5$ | 1.5 × 10$^5$ | |
| 0.05 (0.020) | 24 | 0 | 0 | 0 | |
| | 48 | 1.0 × 10$^5$ | 3.3 × 10$^4$ | 6.3 × 10$^2$ | |
| | 72 | 4.2 × 10$^5$ | 5.4 × 10$^4$ | 1.3 × 10$^3$ | |
| 0.07 (0.028) | 24 | 0 | 0 | 0 | |
| | 48 | 6.2 × 10$^2$ | 0 | 0 | |
| | 72 | 2.0 × 10$^3$ | 0 | 0 | |
| 0.08 (0.032) | 24 | 0 | 0 | 0 | |
| | 48 | 0 | 0 | 0 | |
| | 72 | 0 | 0 | 0 | |
| 0.09 (0.036) 0.1 (0.04) 0.1 (0.08) 0.3 (0.12) 0.4 (0.16) 0.5 (0.20) | 24 | 0 | 0 | 0 | |
| | 48 | 0 | 0 | 0 | |
| | 72 | 0 | 0 | 0 | |
| Dist. H$_2$O | 24 | 4.2 × 10$^7$ | 3.1 × 10$^7$ | 4.3 × 10$^7$ | 8.8 × 10$^7$ |
| | 48 | 4.1 × 10$^7$ | 4.1 × 10$^7$ | 4.3 × 10$^7$ | 8.7 × 10$^7$ |
| | 72 | 3.7 × 10$^7$ | 5.7 × 10$^7$ | 4.2 × 10$^7$ | |

* Wt./vol % formaldehyde concentration in brackets

The greatest concentration of formalin allowing *E. coli* to survive was 0.07–0.08%; above this all were dead. Below 0.02% there was virtually no effect. The degree of survival appears directly related to formalin concentration between 0.02 and 0.08%. Within 0.04 to 0.07% there was a gradual effect related to the time of exposure i.e. the number after 10 hours exceeds the number after 20 hours. It was also evident that the longer the plate counts were postponed the greater the counts became. The P 307 strain was more resistant to formalin that the EW1 but the trends were similar.

Thus a desired balance of effect can be achieved by adjusting the concentration of formalin and the time of exposure for each strain. A plate count of zero at 24 hours but a partial recovery in count at 48–72 hours indicates an upper limit in severity for an acceptable treatment.

Table 2

Number of Colonies of EW1 Strain

| Conc. Formalin % v/v * | Hrs. of Incubation | Hours Incubation with Formalin | | | |
|---|---|---|---|---|---|
| | | 10 | 15 | 20 | 0 |
| 0.01 (0.004) | 24 | 9.2 × 10$^6$ | 2.1 × 10$^7$ | 2.4 × 10$^7$ | |
| | 48 | 1.3 × 10$^7$ | 2.1 × 10$^7$ | 2.5 × 10$^7$ | |
| | 72 | 1.3 × 10$^7$ | 2.3 × 10$^7$ | 2.5 × 10$^7$ | |
| 0.02 (0.008) | 24 | 9.4 × 10$^5$ | 9.5 × 10$^5$ | 8.2 × 10$^5$ | |
| | 48 | 1.6 × 10$^6$ | 9.5 × 10$^5$ | 8.2 × 10$^5$ | |
| | 72 | 1.6 × 10$^6$ | 8.5 × 10$^5$ | 8.5 × 10$^5$ | |
| 0.03 (0.012) | 24 | 2.3 × 10$^5$ | 1.8 × 10$^5$ | 1.8 × 10$^5$ | |
| | 48 | 2.5 × 10$^5$ | 1.9 × 10$^5$ | 1.8 × 10$^5$ | |
| | 72 | 2.6 × 10$^5$ | 1.9 × 10$^5$ | 1.9 × 10$^5$ | |
| 0.04 (0.016) | 24 | 3.0 × 10$^3$ | 2.3 × 10$^3$ | 1.6 × 10$^3$ | |
| | 48 | 9.2 × 10$^3$ | 3.4 × 10$^3$ | 3.5 × 10$^3$ | |
| | 72 | 1.1 × 10$^4$ | 3.2 × 10$^3$ | 3.2 × 10$^3$ | |
| 0.05 (0.020) | 24 | 0 | 0 | 0 | |
| | 48 | 2.0 × 10$^2$ | 11.0×10$^1$ | 1.0 × 10$^1$ | |
| | 72 | 3.9 × 10$^2$ | 2.3 × 10$^2$ | 0 | |
| 0.07 (0.028) | 24 | 0 | 0 | 0 | |
| | 48 | 0 | 0 | 0 | |
| | 72 | 3.2 × 10$^1$ | 0 | 0 | |
| 0.08 (0.032) | 24 | 0 | 0 | 0 | |
| | 48 | 0 | 0 | 0 | |
| | 72 | 0 | 0 | 0 | |
| All Others 0.09 – 0.5 | 24 | 0 | 0 | 0 | |
| | 48 | 0 | 0 | 0 | |
| | 72 | 0 | 0 | 0 | |
| Dist. H$_2$O | 24 | 3.9 × 10$^7$ | 2.5 × 10$^7$ | 3.6 × 10$^7$ | 2.8 × 10 |
| | 48 | 3.9 × 10$^7$ | 2.4 × 10$^7$ | 3.6 × 10$^7$ | — |
| | 72 | 3.9 × 10$^7$ | 2.4 × 10$^7$ | 3.5 × 10$^7$ | 3.0 × 10 |

* Wt./vol. % formaldehyde concentration in brackets

EXAMPLE 2

Strain A1 of serotype 0149:K91; K88a,c:H10 was used to prepare the vaccine. A tryptic soy broth culture containing 7–8 × 10$^8$ viable bacterial/ml. was incubated for 15 hours at 37°C. in the presence of 0.04% v/v of formalin in a closed container. The formolized cultures contained approximately 7 × 10$^6$ viable bacteria/ml. The vaccine was newly prepared for each vaccination. Colony morphology of the formolized bacteria was determined after plating on blood agar plates.

Effect of 0.04% Formalin on the Organism — After the formolized culture was plated on blood agar, bacteria colonies were not visible after 24 hours of incubation at 37°C; however, after 48 hours, colonies of *E. coli* were evident. They were hemolytic and varied considerably in size and differed in varying degrees from the colonies of nonformolized cultures in appearance.

Strain EW1 of 0157, and other strains have also been used to prepare the vaccine in a similar manner. The EW1 strain in particular has been found more susceptible to the formalin and the viable cells remaining are about 2 log dilutions less than for instance the A1 strain.

EXAMPLE 3

One Landrace sow and 12 Yorkshire sows between 12 and 18 months of age at the time of farrowing were used. They were fed a commercial sow ration. Gnotobiotic pigs were produced and reared by the method described by Alexander et al., Gnotobiotic Pigs: Procurement, Microbial Flora, Serum Proteins and Lymphathic Tissues, Canad. Vet. J., 10, (1969) 98–105.

Vaccination — Vaccination was done with a formolized live *E. coli* vaccine prepared as described in Example 2. Five sows were vaccinated intramuscularly in each side of the neck. Five sows were vaccinated by inoculation via the teat canal into the lactiferous duct of a single mammary gland. Each sow was vaccinated 3 times: at 29, 14 and 5 days before farrowing (114 days of gestation); doses of vaccine were 4, 6, and 8 ml., respectively. The same mammary gland in a given sow was inoculated each time. Three sows were used as nonvaccinated controls.

Bacteria — Strain A1 of serotype 0149;K91;K88a,c:H10 was used in preparation of the vaccine inoculated in the sows and was used as the inoculum in the oral challenge exposure of the gnotobiotic pigs.

Approximately 1 l. of colostrum was collected from each sow during parturition. Immediately after collection it was centrifuged at 5,000 g and then held at 4°C for 4 hours to allow the fat to congeal. The non-fat portion was removed and centrifuged for 2 hours at 44,000 g at 22°C to remove casein. The resultant whey was stored at −30°C.

A pooled sample was prepared by mixing equal aliquots of colostral whey from each sow within a treatment group. The pool was clarified by passing it through a prefilter, 3.0, 0.8 and 0.45μ membrane filter pads in series and then sterilized by passing through a sterile 0.22μ membrane filter. The eluant was dispensed in 10 ml aliquots into sterile vacutainers. Sterility of each of the wheys was checked by inoculating two blood plates with 0.5 ml of the filtered whey.

The whey obtained from the sows was used in protection tests against the enteropathogenic effect of E. coli in 10 day old gnotobiotic piglets. Each piglet received one aliquot of colostral whey every 8 hours for 72 hours. Six hours after the first whey sample was given, the piglets were infected orally with 0.2 ml of broth culture containing approximately $8 \times 10^8$ E. coli per ml. The culture was added to the feed.

In this series of experiments 10 ml of the basal feed were replaced with 10 ml of sterile whey.

The survival time from the first whey feeding was recorded for each piglet. Observations were made at the same 8 hour intervals as feeding took place. Surviving piglets were killed 7 days after the first sample application and are recorded as having survived for 168 hours.

From the results of the present experiment, in Table 3 below, the conclusion can be drawn that colostrum from vaccinated sows fed orally to newborn pigs has some protective effect against enteric infections caused by E. coli, whereas colostrum from nonvaccinated, normal sows has no protective value for pigs against experimental exposure to the organism.

TABLE 3

| No. of pigs | Treatment | Mean survival time (Hours) |
|---|---|---|
| 3 | Colostrum from sows vaccinated by intramammary route | 147 |
| 3 | Colostrum for sows vaccinated by intramuscular route | 83 |
| 4 | Colostrum from nonvaccinated sows | 38 |
| 8 | No treatment | 37 |

EXAMPLE 4

E. coli serotype 0149:K91; K88ac:H10 was used for broth vaccine production as in Example 2 and infection purposes.

Five sows were vaccinated intramuscularly, five sows intramammarily and three sows were left as unvaccinated controls. Each sow was vaccinated 28 days prior to the expected farrowing date with 4 ml of the formalinized culture, 6 ml were inoculated 14 days later followed by 8 ml 5 days before the expected farrowing day (114 days of gestation).

Approximately 1 liter of milk was collected from each sow seven days after farrowing. The milk was processed as described in Example 3 for the colostrum. Forty ml of the feed were replaced with processed milk whey. Survival times were recorded as in Example 3.

All of the piglets developed profuse diarrhea 8 to 16 hours after infection; diarrhea continued through the experiments and no differences in severity of diarrhea or rapidity of onset of dehydration were noted between pigs in the different treatment groups.

Table 4 shows the results of the trial in which the piglets were given 40 ml of sows' milk whey. Milk from normal non-vaccinated sows did not prolong the survival time of infected gnotobiotic piglets. In this trial milk from both intramammary and intramuscularly vaccinated sows afforded an increase in survival time when compared to that of piglets in the groups receiving either non-vaccinated sows' milk or condensed cow milk.

Results reported in this Example confirm that protection (reduced mortality) against the enteropathogenic effects of E. coli in pigs can be afforded through the antibodies present in milk, even when fed at very low levels when compared with normal milk intake.

EXAMPLE 5

Quantitatively, IgG constitutes an important immunoglobulin in sows milk. Therefore sufficient IgG was separated from the colostrum of immunized sows to determine its effectiveness in multiplication inhibition, and pig protection tests. The IgG was isolated by a DEAE batch method, and was calculated to have $s_{20} = 6.86$. To complete the tests, 30 g of the pure IgG were isolated.

Table 4

Survival Time of Gnotobiotic Piglets

| Treatment | Source Litter No. | Individual Pig Survival Time (Hours) | Treatment Mean (Hours) |
|---|---|---|---|
| 40 ml of milk whey from sows vaccinated via intramammary route | 72 | 168 | |
| | 72 | 168 | |
| | 76 | 48 | 144 |
| | 78 | 168 | |
| | 78 | 168 | |
| 40 ml of milk whey from sows vaccinated via intramuscular route | 72 | 152 | |
| | 72 | 168 | |
| | 76 | 64 | 118 |
| | 79 | 168 | |
| | 80 | 40 | |
| 40 ml of milk from non-vaccinated sows | 72 | 112 | |
| | 72 | 56 | |
| | 76 | 40 | 61 |
| | 76 | 56 | |
| | 80 | 40 | |
| Control (Condensed cows milk) | 78 | 40 | |
| | 78 | 168 | |
| | 76 | 32 | 62 |
| | 79 | 32 | |
| | 80 | 40 | |

MULTIPLICATION INHIBITION (MI) TESTS

Vaccination of sows with the living, formalinized E. Coli vaccine of the invention has resulted in a marked decrease in their serum bactericidal activity to the vaccine strain. The serum bactericidal activity present in non-vaccinated sows was replaced or masked on vaccination by the development of a MI factor which was distinct from bactericidal antibody in that it was effective in the absence of complement. In the presence of this MI factor the vacnal strain of E. coli multiplied at a very much reduced rate when compared to that in control absorbed serum. Colostrum from the vaccinated sows contained MI factor whereas colostrum from non-vaccinated sows contained neither effective bactericidal antibody or the MI factor. The IgG preparation described herein was found to contain MI factor as is illustrated in Table 5. The test was performed with a solution containing 10 mg/ml of IgG in saline.

PIG PROTECTION TESTS

Fifteen gnotobiotic pigs were divided into three groups of five. At 5 days of age the following daily treatments were instituted and continued for 3 days:
1. One g of IgG from the colostrum of immunized sows in 90 ml of phosphate buffered saline.
2. One g of gamma globulins present in 90 ml of diluted colostrum from immunized sows.
3. Control — 90 ml of phosphate buffered saline.

The treatments, mixed with the regular diet of condensed cow milk, were given in 3 equal doses on each of the 3 treatment days. Observations were made at 8 hourly intervals, at the time of feeding.

A summary of the results is recorded in Table 6.

Significant protection, as indicated by a prolongation of survival time, was afforded by both colostrum from immunized sows and by IgG isolated from that colostrum.

TABLE 5

The effect of colostrum and colostral IgG from vaccinated sows on the multiplication of the homologous vaccinal strain.

| Sows* | Hours of Incubation | Mean No. of CFU $\times 10^3$ | | |
|---|---|---|---|---|
| | | Colostral Whey | | IgG |
| Vaccinated | 0 | 86 | | 80 |
| | 3 | 252 | | 149 |
| Non-Vaccinated | 0 | 90 | | 75 |
| | 3 | 1953 | | 4652 |
| Saline | 0 | | 85 | |
| | 3 | | 2597 | |

*Six samples tested in each group

TABLE 6

Survival times of gnotobiotic pigs infected with serotype 0149:K91 K88ac:H10 *Escherichia coli* and fed colostrum or colostral IgG from sows.

| Daily Treatment | No. of Pigs | Mean Survival Time in Hours |
|---|---|---|
| 1 gram of Gamma Globulin (In colostral whey frm immunized sows) | 5 | 90 (12.4) |
| 1 gram of IgG from from colostrum from immunized sows) | 5 | 96 (11.75) |
| Phosphate Buffer Saline | 5 | 45 ( 8.25) |

( ) = Standard deviation

EXAMPLE 6

In field trials, 120 sows have been vaccinated, 33 by the intramuscular and 87 by the intramammary route, 87 non-vaccinated control sows having been kept. The sows were on 2 commercially-operated farms which were chosen because of their having a persistent and high incidence of neonatal diarrhea.

HERD 1. consisted of approximately 110 sows of predominantly Yorkshire type. Pigs in almost all litters developed diarrhea between 2 and 5 weeks of age. Pure cultures of *E. coli* serogroup 0138 were isolated on several occasions, and a homologous vaccine was prepared from the P 570 strain of 0138. The sows were listed according to farrowing dates and divided into replicates of 3. Each replicate consisted of a sow vaccinated into a single mammary gland with 2 ml of the vaccine, another vaccinated intramuscularly and a third left unvaccinated.

HERD 2. A herd of 120 hybrid, predominantly Yorkshire type sows. Pigs in all litters developed diarrhea between 3 and 5 weeks of age. Pure cultures of *E. coli* serogroup 0157 were isolated from several pigs. A heterologous vaccine, prepared from a non-pathogenic (in gnotobiotic pigs), lab variant of *E. coli* serogroup 08 (P307) was used in this herd. Equal numbers of sows were vaccinated into the mammary gland as were left as unvaccinated controls. Two ml of the vaccine was inoculated into a single mammary gland.

Each farm was visited once a week for vaccination, the sows were vaccinated 3 times, in the periods 24–31, 10–17 and 3–10 days before farrowing.

Table 7 is a summary of the results obtained.

The practice in each herd was to treat all pigs in the litter if severe diarrhea occured; the results are presented, therefore, as the number of litter treatments necessitated by the onset of diarrhea. Almost four times as many litter treatments were needed in the control sow litters as were needed in litters of vaccinated sows. Both intramuscular and intramammary routes of vaccine administration significantly reduced the number of treatments necessary per weaned litter compared to that needed in litters of non-vaccinated sows ($P<0.05$). Similarly, diarrhea recurred in litters of non-vaccinated sows on significantly more occasions than in litters of sows of either vaccinated groups ($P<0.05$).

As can be seen from Table 7, in the first 10 sows on each farm in each treatment group the incidence of diarrhea was lower in the vaccinated than non-vaccinated sow litters. At the end of the trial the incidence had dropped in the non-vaccinated as well as the vaccinated sow progeny. This is thought to be associated with a reduction in the infection "load" of the farrowing area.

TABLE 7

| Vaccination | Number of Litter treatments | |
|---|---|---|
| | First 10 litters | Last 10 litters |
| HERD No. 1 | | |
| None (control) | 13 | 2 |
| Intramammary | 2 | 1 |
| intramuscular | 1 | 1 |
| HERD No. 2 | | |
| None (control) | 21 | 0 |
| intramammary | 5 | 0 |

EXAMPLE 7

Four pregnant cattle of the Jersey breed were used, At the time of calving each cow was approximately 2 years of age. The *E. coli* strains used for vaccine production are designated A1 and P307. Strain A1 is an enteropathogen of pigs with the serological formula 0149:K91;88ac:H10. Strain P307 is a swine enteropathogen with the antigenic formula 08:K87;88ab:H19. The live formalinized *E. coli* vaccine was prepared as described in Example 2. Vaccine was introduced into the teat cistern of the left hind (LH) and right front (RF) mammary glands via the teat canal. Heifer 2Z was vaccinnated with an antigen prepared from the P307 *E. coli* strain: 4 ml and 6 ml were inoculated into each gland 15 and 5 days before calving respectively. Heifer 4Z was vaccinated with the P307 antigen: 4 ml, 6 ml, 8 ml were inoculated into each gland 42, 32, 22 and 12 days before calving respectively. Heifer W4 was vaccinated with an antigen prepared from the A1 strain of *E. coli:* 4 ml, 6 ml, and 8 ml were inoculated into each gland 26, 16 and 6 days before calving respectively. Heifer 6Z was vaccinated with A1 antigen: 4 ml, 6 ml and 5, 8 ml doses were inoculated into each gland 95, 85, 75, 65, 55, 45 and 35 days before calving respectively.

Colostrum was taken from each gland on the day that calving occurred and milk from each gland on 2, 3, 4, 7, 14 and 28 days after calving. Further samples were taken from cow 4Z on days 42 and 56: this cow was retained until she had calved again 455 days after the last vaccination. Whey was prepared from the colostrum and milk sampled by centrifugation at 44,000 g for 2 hours. The whey was stored in 2 ml aliquots at $-30°$.

The samples taken on days 1 and 2 after calving from cows vaccinated with a vaccine prepared from the A1 strain of *E. coli*, showed an almost complete lack of multiplication when tested against A1 organisms. This bacteriostasis was evident in all samples taken up to 4 days after calving in the milk whey from cow 6Z, thereafter bacterial multiplication took place, but to a much greater extent in the whey from non-vaccinated glands than in whey from vaccinated glands. Bacterial multiplication took place in whey from non-vaccinated glands of cow W3 on the third day after calving but was not evident in samples from vaccinated glands until the 14th day after calving. There was an approximate 10-fold difference between the colony count from vaccinated and non-vaccinated gland whey samples from both 6Z and W3 on days 7, 14 and 21 post calving. This difference between vaccinated and non-vaccinated glands was less pronounced, but still significant, in samples taken on the 28th day after calving. ($P<0.001$).

The whey samples from cows vaccinated with the P307 strain (4Z and 2Z) differed in their response in the antibacterial test from the samples from A1 vaccinated cows. Bacterial multiplication occurred in colostral whey and in all samples taken thereafter. There was no obvious reductions in the multiplication rate of bacteria in test samples from vaccinated compared to non-vaccinated glands until day 4. This reduction in multiplication rate persisted and was clearly evident in samples taken from vaccinated glands from cow 4Z taken on day 28, but was statistically significant only on days 4, 7 and 14 ($P<0.05$).

Indirect hemagglutinating antibody titres in milk from vaccinated and non-vaccinated mammary glands.

The hemagglutinating antibody titres found in milk after intramammary vaccination of 2 of the 4 glands were measured. The titres in colostrum from the inoculated glands (RF and LH) were from 2 to 4 times that found in milk from the non-inoculated glands. The average titre in milk taken from the vaccinated glands 7 days after calving was approximately 7 times that found in milk from the non-inoculated glands and by 28 days after calving there was a 14 fold difference in antibody titres between the vaccinated and non-vaccinated gland milk samples. On the 28th day after calving, the average indirect hemagglutinating antibody titre in milk from the non-vaccinated glands was 1/50th of that found in colostrum from the same glands, whereas, the titre in milk from vaccinated glands was 1/11th of that in colostrum from the vaccinated glands. A milk sample from the secreting vaccinated gland of one cow (4Z) 56 days after calving, still had a titre of 1:64, whilst, no indirect hemagglutinating antibodies were demonstrable in milk taken from the non-vaccinated glands 35 days after calving.

Cow 4Z was retained and calved again 455 days after the last vaccination. The indirect hemagglutinating antibody titre in the second lactation colostral and milk whey from the vaccinated gland was four times that in whey from non-vaccinated glands. All titres were considerably lower than in the previous lactation.

PROTECTION TESTS

Six day old gnotobiotic pigs, derived from one sow, were infected with $10^8$ organisms of the A1 strain of *E. coli* and fed 100 ml of milk whey 3 times daily for 3 days. The whey was prepared from milk obtained between 7 and 14 days after calving from the vaccinated cows described earlier, and from a non-vaccinated cow. Whey from each of the three sources (A1 and P307 vaccinated, and non-vaccinated) was fed to 5 pigs.

Observations were recorded at 8 hour intervals and survival times determined from the time of infection were compared using the paired t test. The pairs were formed from the treatment within each isolator.

The results of the protection test are presented in Table 8. The survival time of the pigs receiving milk from non-vaccinated cows was significantly shorter than that of pigs in either of the groups being fed milk from vaccinated cows. ($P<0.05$).

Protection was afforded against the pathogenic effects of the *E. coli* serogroup A1 by milk from homologously vaccinated cows and by milk from cows vaccinated with the heterologous *E. coli*.

TABLE 8

Survival times (Hours) of gnotobiotic piglets fed milk whey from vaccinated or non-vaccinated cows

| Isolator No. | No. of pigs | Whey Non Vaccinated | Vaccinated P307 | Vaccinated A1 |
|---|---|---|---|---|
| 1 | 4 | 62 | 46.102 | 110 |
| 2 | 4 | 38 | 46 | 54.118 |
| 3 | 4 | 38.62 | 62 | 62. |
| 4 | 3 | 46 | 94 | 70 |
| Mean | | 49 | 70 | 83 |
| Standard Deviation | | 11 | 24 | 26 |

EXAMPLE 8

In another trial in progress 4 of 7 pigs being fed milk from non-vaccinated cows died from *E. coli* infection, while only 1 of 5 being fed reconstituted spray-dried milk from cows vaccinated with 0157 strain died, and none of 5 fed reconstituted milk from cows vaccinated with the A1 strain of 0149; K91, K88a,c:H10. In all cases the pigs were challenged with the A1 strain.

Three strains of *E. coli* from human sources have been used to prepare vaccines according to the invention. These vaccines were used to vaccinate heifers and the milk recovered. It was noticed that calves from the vaccinated heifers did not contract infection whereas calves from 12 contemporary heifers did contract infection and 5 of these 12 died.

EXAMPLE 9

Further field trials have been carried out in four swine herds using the vaccine of the invention. The herds were divided into control (unvaccinated) and vaccinated groups. The mortality of piglets from the control and vaccinated sows was followed. The results are summarized in Table 9.

TABLE 9

| Herd | | No. of Litters | Aver. No. Born per Litter | No. alive at 21 days per litter | % Survival |
|---|---|---|---|---|---|
| A | Controls | 17 | 10.8 | 8.0 | 74% |
|   | Vaccinated | 17 | 10.8 | 9.1 | 84% |
| B | Controls | 16 | 10.7 | 8.4 | 79% |
|   | Vaccinated (IM)* | 25 | 10.2 | 8.5 | 83% |
| C | Controls | 34 | 10.7 | 8.3 | 77% |
|   | Vaccinated (IM)* | 33 | 10.3 | 8.5 | 83% |
|   | (IMa)** | 34 | 11.1 | 8.8 | 79% |
| D | Controls | 53 | 10.1 | 8.0 | 79% |
|   | Vaccinated (IMa)** | 54 | 10.5 | 8.7 | 83% |

*IM = intramuscular
**IMa = intramammary

Herd A had no diarrhea but diarrhea was present in the other 3 herds. These results show a significant increase in surviving piglets per litter or % survival where vaccination was carried out — even where there was no evidence of *E. coli* infection in the herd.

I claim:

1. A method of protecting or treating newborn swine subject to *E. coli* infections comprising:
   a. recovering milk from milk cows vaccinated intramammarily into the test cistern while pregnant with the bacterial vaccine comprising a live strain or strains of selected *E. coli* pathogenic to swine incubated in and modified by dilute solutions of about 0.02 to about 0.08% v/v formalin to give an altered growth pattern and appearance and reduced viable cell count; and
   b. continually feeding the piglets with said milk or protective, antibody-containing fraction thereof having antibody titers effective against said infections, for the period of protection or treatment required.

2. A dried milk composition or protective, antibody-containing fraction thereof having antibody titers effective in swine against *E. coli* infections, obtained from cows vaccinated intramammarily into the teat cistern while pregnant with the *E. coli* vaccine comprising a live strain or strains of selected *E. coli* pathogenic to swine incubated in and modified by dilute solutions of about 0.02 to about 0.08% v/v formalin to give an altered growth pattern and appearance and reduced viable cell count.

3. The composition of claim 2 in the form of dried whey.

4. The method of claim 1 wherein vaccination is carried out at least twice to increase antibody titers.

5. The composition of claim 2 from cows vaccinated at least twice to increase antibody titers.

* * * * *